United States Patent [19]

Edmundowicz et al.

[11] 4,354,971
[45] Oct. 19, 1982

[54] NON-EXTRACTIVE PENICILLIN V RECOVERY PROCESS

[75] Inventors: John M. Edmundowicz, Carmel; Ernest E. Allanson, Brownsburg, both of Ind.

[73] Assignee: Eli Lilly and Company, Indianapolis, Ind.

[21] Appl. No.: 276,446

[22] Filed: Jun. 22, 1981

[51] Int. Cl.$^3$ ............... C07D 499/18; C07D 499/20; C07D 499/16; C07C 51/50
[52] U.S. Cl. .................................. 260/239.1; 562/471
[58] Field of Search ..................... 260/239.1; 562/471

[56] References Cited

U.S. PATENT DOCUMENTS

| | | | |
|---|---|---|---|
| 2,756,226 | 7/1956 | Brandl et al. | 260/239.1 |
| 3,461,116 | 8/1969 | Nahm et al. | 260/239.1 |
| 3,502,655 | 3/1970 | Oppinger et al. | 260/239.1 |
| 3,904,605 | 9/1975 | Baker | 260/239.1 |

FOREIGN PATENT DOCUMENTS 1131677  9/1959  Fed. Rep. of Germany.

Primary Examiner—Natalie Trousof
Assistant Examiner—Vera C. Clarke
Attorney, Agent, or Firm—Dwight E. Morrison; Arthur R. Whale

[57] ABSTRACT

Non-extractive process for the separation and purification of penicillin V from fermentation broth by addition of acid to acid-polished fermentation broth.

14 Claims, No Drawings ined as with aqueous acid, preferably aque-

NON-EXTRACTIVE PENICILLIN V RECOVERY PROCESS

SUMMARY

This invention relates to a non-extractive process for the separation and purification of penicillin V acid directly from the fermentation broth, and the isolation of the potassium salt of penicillin V acid.

BACKGROUND OF THE INVENTION

Historically, the recovery of pencillins from the whole fermentation broth has included, as the primary purification step, a solvent extraction of the penicillins directly from the filtered fermentation broth. Both theory and practice (especially under controlled laboratory conditions) have shown this procedure to be highly efficient and selective.

In the case where the penicillins produced in the fermentation are stable to acid, the fermentation broth is adjusted to an acid pH before the extraction with the organic solvent. The acid-stable penicillin present in the organic phase is then transferred to an aqueous buffer solution, from whence it can then be crystallized by salting out of solution with a salt such as potassium acetate.

This remarkable stability to acids displayed by certain penicillins has long been known in the art. Brandl et al., U.S. Pat. No. 2,756,226 (July 24, 1956), teach that these penicillin acids can be recovered from an aqueous solution of their salts simply by acidifying the solution and filtering off the solid crystalline penicillin acid which precipitates. Among the acids disclosed in this reference is phenoxymethyl penicillin, i.e., penicillin V. German Pat. No. 1,131,677 teaches the purification of phenoxymethyl penicillin, as an alkali of ammonium salt, by acidification with excess of acetic acid to give yields of up to about 90 percent of the pure penicillin acid. Further, Baker, U.S. Pat. No. 3,904,605 (Sept. 9, 1975), discloses a process for preparing penicillin sulfoxides starting with penicillin-containing, filtered fermentation broth. After formation, the penicillin sulfoxide is precipitated by the addition of acid.

The separation of a penicillin in the form of its potassium salt from a butyl acetate extract of filtered fermentation broth, by the addition of a 20% solution of anhydrous potassium acetate in methanol, is disclosed by U.S. Pat. No. 3,461,116 (Aug. 12, 1969), and U.S. Pat. No. 3,502,655 (Mar. 24, 1970).

It is well-known to those skilled in the penicillin art that conventional extraction procedures involving water-immiscible solvents are multi-step, and, in general, costly to operate. The presently disclosed process overcomes this disadvantage of the older method.

Another advantage of the instantly disclosed novel process is that the inention makes it possible to process fermentation broths which contain large excesses of residual precursor. The precursor in the case of penicillin V is phenoxyacetic acid, usually employed as the sodium salt. The acidification process also assits in removing insolubles and mycelial solids, some amorphous and microcrystalline substances, and in the case of penicillin V, an impurity identified as p-hydroxy penicillin V, since the latter, together with phenoxyacetic acid, remains in the liquid phase after the acidification.

DETAILED DESCRIPTION

The present invention provides a novel, non-extractive process for the recovery of penicillin V acid directly from the fermentation broth, that is, the penicillin whole broth, and the isolation of the penicillin V acid as its potassium salt. This invention thus provides a simplified procedure for the efficient and economical recovery of penicillin V, an important item of commerce, directly from the fermentation broth. Further, the penicillin V thus obtained is of excellent pharmaceutical quality. This process is also broadly applicable to the other acid-stable penicillins.

The novel process can be described as a combination of a series of steps and the various steps are recited below as a convenient means for describing the best mode of the process contemplated by us at the present time. This process comprises:
  a. adjustng the whole broth to a pH between about 4.0 and about 4.3 with aqueous acid while maintaining the temperature of the broth in the range from about 15° to about 30° C., and separating the acidified liquid phase from insolubles;
  b. adjusting the liquid phase to a pH between about 2.0 and about 2.5 with dilute aqueous acid, with stirring;
  c. separating the penicillin V acid crystals from the mixture of Step (b); and
  d. dissolving the crystalline penicillin V acid crystals of Step (c) in a organic solvent, adding potassium 2-ethyl hexanoate, and separating the potassium salt of penicillin V acid from the mixture.

The potassium salt of penicillin V acid can be further purified by recrystallization from water or by salting it out from an aqueous solution by the use of potassium acetate, by procedures well-known in the penicillin art.

Alternatively, the whole fermentation broth can be filtered prior to the first acidification, thus removing the bulk of the mycelia before the first acidification. The process is described as a combination of the following series of steps:
  a. filtering the penicillin whole broth;
  b. adjusting the filtered broth to a pH between about 4.0 and about 4.3 with aqueous acid, while maintaining the temperature of the broth in the range from about 15° to about 30° C., adding filter aid, and filtering the mixture;
  c. adjusting the filtrate to a pH between about 2.0 and about 2.5 with dilute aqueous acid, with stirring;
  d. separating the penicillin V acid crystals from the mixture of Step (c); and
  e. dissolving the crystalline penicillin V acid crystals of Step (d) in an organic solvent, adding potassium 2-ethyl hexanoate, and separating the potassium salt of penicillin V acid from the mixture.

The potassium salt of penicillin V acid can be further purified as described above.

Because one filtration step is eliminated, the first process described above is the preferred embodiment of the hereindisclosed invention.

In the practice of this invention according to the preferred embodiment, whole fermentation broth is adjusted to a pH between about 4.0 and about 4.3, suitably about pH 4.2, using aqueous acid, preferably aqueous sulfuric acid, at a concentration of about 30 percent, while maintaining the temperature of the whole broth in the range from about 15° to about 30° C. Other acids suitable for use in this acidification include citric, phosphoric, hydrochloric, nitric, or one of the arylsulfonic acids, for example, benzenesulfonic acid, toluenesulfonic acid, a halo-substituted phenylsulfonic acid such as p-chlorophenylsulfonic acid, naphthalenesulfonic acid, and like aryl and substituted arylsulfonic acids. This acidification aids in removing the mycelia, certain insoluble inorganic salts (mainly calcium sulfate), proteinaceous materials, and residual media ingredients such as soya flour. The acidified whole fermentation broth is then filtered, and the material collected on the filter washed with water. The combined filtrate and water washings are again acidified, this time to a pH between about 2.0 and about 2.5, using dilute aqueous acid, e.g., 10% aqueous sulfuric acid, and the mixture stirred for a period of time, suitably about 30 minutes, while the penicillin V acid crystals form.

After crystallization is complete, the penicillin acid crystals are easily recovered by centrifugation or filtration. Excess precursor, i.e., phenoxyacetic acid, and other acid soluble impurities, such as p-hydroxy penicillin V, remain in the liquid phase after removal of the penicillin V acid crystals. The crystals take the form of dense rosettes which settle out of the slurry fairly rapidly, and range in color from off-white or light tan to dark brown, depending upon the quality of the broth. After the crystals are harvested, they are washed thoroughly with water to remove residual acid. Acid-free crystals of penicillin V are conveniently obtained by washing the crystals with a volume of water corresponding to approximately 20% of the polished broth volume. The penicillin V acid crystals thus obtained are desirably dried prior to proceeding to the next step of the process. The drying is suitably accomplished in vacuo in an oven at a temperature of 45°–50° C. over a period of approximately 40 hours.

The dry penicillin V acid is then dissolved in an organic solvent such as acetone or isopropyl alcohol, with acetone being the solvent of choice. The solvent should be essentially anhydrous, as the presence of water, even in a small amount, greatly suppresses the yield. The acetone solution is decolorized by passing the acetone solution of the penicillin V acid over a column of decolorizing carbon. To the acetone solution is then added the potassium salt of an organic acid, the anion of which has good solubility in the acetone. Such acids include linear or branched-chain acids in a homologous series from butanoic up through octanoic, with 2-ethyl hexanoic being the acid of choice. Thus, there is added to the acetone solution 1.2 molar equivalents of potassium 2-ethyl hexanoate, with stirring at ambient temperature, and the potassium salt of penicillin V acid which separatres is recovered by filtration.

The further purification and separation of the potassium salt of penicillin V is accomplished by dissolving that salt, obtained above, in water and adding 1.2 weight equivalents of potassium acetate, whereby the pure potassium salt of penicillin V separates and is recovered.

In the practice of the alternative embodiment of the invention, instead of acidifying the whole penicillin broth directly, it is also possible, and suitable, if so desired, to filter the broth first to remove the mycelia. Such filtration is accomplished by methods known in the art, and the mycelial filter cake is washed well with water and the washings added to the filtrate.

This filtrate is then acidified to "polish" it, that is, remove any mycelial fragments or other amorphous or microcrystalline substances remaining in the broth after filtration of the whole fermentation broth. This polishing step is best accomplished by the direct addition of an aqueous acid to the filtered broth until the pH measures between about 4.0 and about 4.3, preferably pH 4.2. Suitable acids include citric, phosphoric, sulfuric, hydrochloric, nitric, or one of the arylsulfonic acids, for example, benzenesulfonic acid, toluenesulfonic acid, a halo-substituted phenylsulfonic acid such as p-chlorophenylsulfonic acid, naphthalene sulfonic acid, and like aryl and substituted arylsulfonic acids. The aqueous acid preferred for use in this step is aqueous sulfuric acid at a concentration of about 30%. As in the preferred embodiment of this invention, the temperature of the broth during the acidification should be maintained in the range from about 15° to about 30° C.

After the aqueous acid has been added, about five minutes of stirring is required to completely precipitate soluble impurities. A filter aid, for example, Standard Super Cel (diatomaceous earth, Johns-Manville Corporation) is then added and the suspension is filtered, and the filter cake on the funnel (or the filter press) is washed with a small (for example 10–15 percent) volume of water. The combined filtrate and wash is identified as polished broth.

In the next step of the process, the polished broth is held at a temperature of about 10°–30° C., preferably at about 20°–25° C., while dilute aqueous acid is added until the pH of the mixture measures between about 2.0 and about 2.5. Any one of the acids mentioned above is suitable for use in this acidification, although dilute aqueous sulfuric acid, i.e., 10 percent v/v, is the acid of choice. About 20–30 minutes of stirring is required for the penicillin V acid to achieve its crystalline form. Cooling the mixture before acidification or after crystallization is complete does not improve the yield of penicillin V acid in this embodiment. The potassium salt of the penicillin V acid is then prepared as described hereinabove, using the potassium salt of a linear or branched chain organic acid selected from the group consisting of the homologous series from butanoic up through octanoic. Potassium 2-ethyl hexanoate is the potassium salt of choice.

The invention will be more fully understood from the following operating examples:

EXAMPLE 1

A portion of whole fermentation broth (pH=6.1) containing 99.48 g. of penicillin activity was adjusted to pH 4.2 with 30% aqueous sulfuric acid. The acidified mixture was filtered and the cake washed with water. The combined filtrate and water washings, containing 89.68 gm. of penicillin activity (90.15% step yield), were acidified to pH 2.0, using 10% aqueous sulfuric acid, and the mixture was stirred for about 30 minutes. The mixture was filtered and the penicillin V acid crystals washed with water. The crystals were then dried at 50° C. The dry crystals weighed 80.0 g.

The dry, crystalline penicillin V acid, 80.0 g., was dissolved in acetone and clarified by filtration. Polarimetric assay of the clarified acetone solution indicated a recovery of 69.3 g. of penicillin, for a step yield of 77.3%. The insoluble material collected on the filter was washed with acetone and the washings combined with the original filtrate. The combined filtrate was then passed over a column containing 35 g. of decolorizing carbon (Pitt CAL), the column being washed with additional acetone. There was obtained an acetone solution containing 60.8 g. of penicillin V acid.

To this acetone solution of 60.8 g. of penicillin V acid there was added 1.2 molar equivalents of an acetone solution of potassium 2-ethyl hexanoate containing a minimum amount of water, and the resulting mixture stirred at ambient temperature for about 60 minutes. The crystalline precipitate, the potassium salt of penicillin V acid, was recovered by filtration and washed with about 250 ml. of acetone. The wet potassium salt was held in the refrigerator overnight.

This wet potassium salt of penicillin V acid was dissolved in distilled water. An assay of the solution indicated the presence of 58.0 g. of penicillin V acid. To this solution was added 1.2 weight equivalents of a saturated aqueous solution of potassium acetate, with stirring for about 90 minutes. The mixture was then cooled to a temperature of 10° C. for about 40 minutes. The crystalline potassium salt of penicillin V acid was recovered by filtration, and washed on the filter with about 250 ml. of isopropyl alcohol. The crystals, after drying at 50° C., weighted 61.6 g. Step yield=91.99%. Overall yield from whole broth=56.22%.

EXAMPLE 2

(a) Preparation of Polished Broth

To a portion of production filtered broth containing 62.5 g. of phenoxymethyl penicillin, there was slowly added with stirring a 30 percent v/v aqueous sulfuric acid solution until the pH of the mixture measured 4.2. The mixture was stirred for several minutes, 50 g. of filter aid (diatomaceous earth, Standard Super Cel, Johns-Manville Corporation) was added and the mixture filtered on a large Büchner funnel. The filter cake on the funnel was washed with a small volume of water. The combined filtrate and wash contained 62.4 g. of penicillin V activity. The step yield was 99.8 percent.

Ths procedure was repeated on a larger scale, as follows:

A portion of production filtered broth containing 17.683 kg. of penicillin V activity was acidified to a pH of 4.25 with 30 percent aqueous sulfuric acid. Filter acid (diatomaceous earth, Standard Super Cel, Johns-Manville Corporation), 15.0 kg., was added to the mixture and the mixture was then filtered through a 24-inch plate and frame press. The press cake was washed with 200 liters of deionized water. The combined filtrate and wash contained 17.62 kg. of penicillin V activity, and the step yield was 99.7 percent.

(b) Penicillin V Acid from Polished Broth

Polished broth, pH 4.3, containing 12.344 kg. of penicillin V activity, was acidified to pH 2.2 with 10 percent aqueous sulfuric acid. After stirring for about 45 minutes, the penicillin V acid crystals were harvested on a Tolhurst basket centrifuge and washed with 230 liters of deionized water. The crystals were dried in a vacuum oven at 45° for approximately 40 hours. Polarimetric assay of an acetone solution of the dry crystals indicated that 10.96 kg. of penicillin activity were recovered. The purity of the penicillin V acid crystals was 89.3 percent. The recovery yield from polished broth was 88.8 percent.

The potassium salt of the penicillin V acid is then prepared as described in Example 1.

The following example demonstrates the efficacy of the removal of the precursor by the nonextractive process compared to removal of the precursor by the aqueous crystallization process of the prior art.

EXAMPLE 3

(a) Acid Process with Added Precursor

To a portion of filtered fermentation broth containing 45.39 g. of penicillin activity, there was added 9.0 g. of sodium phenoxy acetate (precursor), and the mixture adjusted to pH 4.2 with 30% aqueous sulfuric acid. The acidified mixture was filtered. The filtrate was adjusted to pH 2.1 with 10% aqueous sulfuric acid and stirred for 30 minutes. The crystalline penicillin V acid which separated was recovered by filtration and washed with water. The penicillin V acid, when dried, weighed 41.8 g.

The dry penicillin V acid was dissolved in acetone and Celite 545 (diatomaceous earth, Johns-Manville Corp.) was added. The mixture was filtered and the filter cake washed with acetone. The filtrate and washings were combined. They contained 36.6 g. of penicillin activity. To the thus obtained acetone solution of penicillin V acid, 1.2 molar equivalents of potassium 2-ethyl hexanoate was added as a 48% aqueous acetone solution, and the mixture stirred for a period of about 60 minutes. The mixture was filtered to recover the potassium salt of penicillin V acid, and the salt crystals on the filter washed with acetone. The product was dried. It weighed 39.8 g., a 79% yield. High performance liquid chromatography of a sample of the product established the presence of 864.4 mcg./mg. of penicillin V and no sodium phenoxy acetate.

(b) Aqueous Crystallization With Added Precursor

To a portion of filtered fermentation broth containing 45.39 g. of penicillin activity, there was added 9.0 g. of sodium phenoxyacetate (precursor), followed by 100 ml. of Demulso (a de-emulsifying agent manufactured by the Tretolite Division of the Petrolite Co., St. Louis, Mo.) and 1000 ml, of isobutyl acetate. The mixture was adjusted to pH 2.0 using aqueous sulfuric acid and then chilled to about 10° C. for about 3 hours. The aqueous layer was separated and discarded. The isobutyl acetate layer, which contained the antibiotic activity, had a volume of about 1000 ml., and was extracted at pH 6.8 with an aqueous carbonate buffer solution.

To the extracts, which contained about 41.6 g. of penicillin activity, there were added 10 ml. of isopropyl alcohol, followed by 2.0 weight equivalents of potassium acetate, added as a saturated aqueous solution. At the end of 60 minutes, the crystalline potassium salt of penicillin V acid was recovered by filtration, washed with isopropyl alcohol, and dried in vacuo at 40° C. for 16 hours. The product weighed 45.1 g. By high performance liquid chromatography, it was determined that the product contained 756.2 mcg./mg. of penicillin V, and 112.2 mcg./mg. of sodium phenoxy acetate.

We claim:

1. A method for recovering penicillin V acid from penicillin V-containing fermentation broth which comprises:
   a. adjusting said broth of a pH of between about 4.0 and about 4.3 while maintaining the temperature of the broth in the range from about 15° to about 30° C.;
   b. separating the acidified liqid phase from insolubles; and
   c. acidifying the liquid phase to a pH of between about 2.0 and about 2.5.

2. The process of claim 1 wherein, in Step (a), whole broth is employed.

3. The process of claim 1 where, in Step (a), filtered broth is employed.

4. The process of claims 1, 2 or 3 where, following Step (c), the penicillin V acid is separated from the liquid phase.

5. The method of claim 1 wherein the acid employed in Step (a) to adjust the pH is 30% aqueous sulfuric acid.

6. The method of claim 1 wherein the acid employed in Step (b) is 10% aqueous sulfuric acid.

7. A method for isolating penicillin V acid potassium salt from penicillin V-containing fermentation broth which comprises:
  a. adjusting the pH of said broth to a pH of from about 4.0 to about 4.3 with aqueous acid while maintaining the temperature of the broth in the range from about 15° to about 30° C., and filtering;
  b. adjusting the filtrate to a pH of from about 2.0 to about 2.5 with dilute aqueous acid, with stirring;
  c. separating the penicillin V acid crystals from the mixture of Step (b); and
  d. dissolving the crystalline penicillin V acid crystals in an organic solvent, adding potassium 2-ethyl hexanoate, and separating the potassium salt of penicillin V acid from the mixture.

8. The method of claim 7 wherein the acid employed in Step (a) is 30% aqueous sulfuric acid.

9. The method of claim 7 wherein the acid employed in Step (b) is 10% aqueous sulfuric acid.

10. The method of claim 7 wherein the organic solvent employed in Step (d) is acetone.

11. A method for preparing penicillin V acid potassium salt which comprises dissolving crystalline penicillin V acid in an organic solvent, adding potassium 2-ethyl hexanoate, and separating the potassium salt of penicillin V acid from the mixture.

12. The method of claim 11 wherein the organic solvent is acetone.

13. A method for separating excess precursor, phenoxyacetic acid, from penicillin V in penicillin V-containing fermentation broth which comprises:
  a. adjusting said broth to a pH of between about 4.0 and about 4.3 while maintaining the temperature of the broth in the range from about 15° to about 30° C.;
  b. separating the acidified liquid phase from insolubles;
  c. acidifying the liquid phase to a pH of between about 2.0 and about 2.5; and
  d. separating the precursor-containing liquid phase from the penicillin V acid crystals.

14. A method for separating p-hydroxy penicillin V from penicillin V in penicillin V-containing fermentation broth which comprises:
  a. adjusting said broth to a ph of between about 4.0 and about 4.3 while maintaining the temperature of the broth in the range from about 15° to about 30° C.;
  b. separating the acidified liquid phase from insolubles;
  c. acidifying the liquid phase to a pH of between about 2.0 and about 2.5; and
  d. separating the p-hydroxy penicillin V-containing liqid phase from the penicillin V acid crystals.

* * * * *